US00PP36022P3

(12) United States Plant Patent
Conev et al.

(10) Patent No.: US PP36,022 P3
(45) Date of Patent: Jul. 23, 2024

(54) SHRUB ROSE PLANT NAMED 'VLR12062'

(50) Latin Name: *Rosa hybrida*
Varietal Denomination: VLR12062

(71) Applicants: Vineland Research and Innovation Centre, Vineland Station (CA); Canadian Nursery Landscape Association, Milton (CA)

(72) Inventors: Rumen Conev, Vineland Station (CA); Parminderjit Sandhu, Vineland Station (CA)

(73) Assignees: VINELAND RESEARCH AND INNOVATION CENTRE, Vineland Station (CA); CANADIAN NURSERY LANDSCAPE ASSOCIATION, Milton (CA)

( * ) Notice: Subject to any disclaimer, the term of this patent is extended or adjusted under 35 U.S.C. 154(b) by 0 days.

(21) Appl. No.: 18/143,926

(22) Filed: May 5, 2023

(65) Prior Publication Data

US 2024/0196768 P1 Jun. 13, 2024

(51) Int. Cl.
*A01H 5/02* (2018.01)
*A01H 6/74* (2018.01)

(52) U.S. Cl.
USPC ..... Plt./102

(58) Field of Classification Search
USPC ..... Plt./101, 102, 104
See application file for complete search history.

(56) References Cited

PUBLICATIONS https://www.bronandsons.com/products/line/flowering-shrubs-roses/gumball-goody-rose-14872. Retrieved from the Internet Nov. 30, 2023.*

* cited by examiner

*Primary Examiner* — Susan McCormick Ewoldt
(74) *Attorney, Agent, or Firm* — Penny J. Aguirre

(57) ABSTRACT

A new cultivar of *Rosa* plant named 'VLR12062' that is characterized by its flowers that are yellow in color with margins that are light pink in color and may become suffused with red when grown in cold temperatures, its flowers that are medium in size, its semi-double flowers, its mildly fragrant flowers, its upright, bushy plant habit, its foliage that is slightly glossy and dark green in color, its good resistance to black spot disease, and its cold hardiness at least to U.S.D.A. Zone 4.

3 Drawing Sheets

Figure 1:
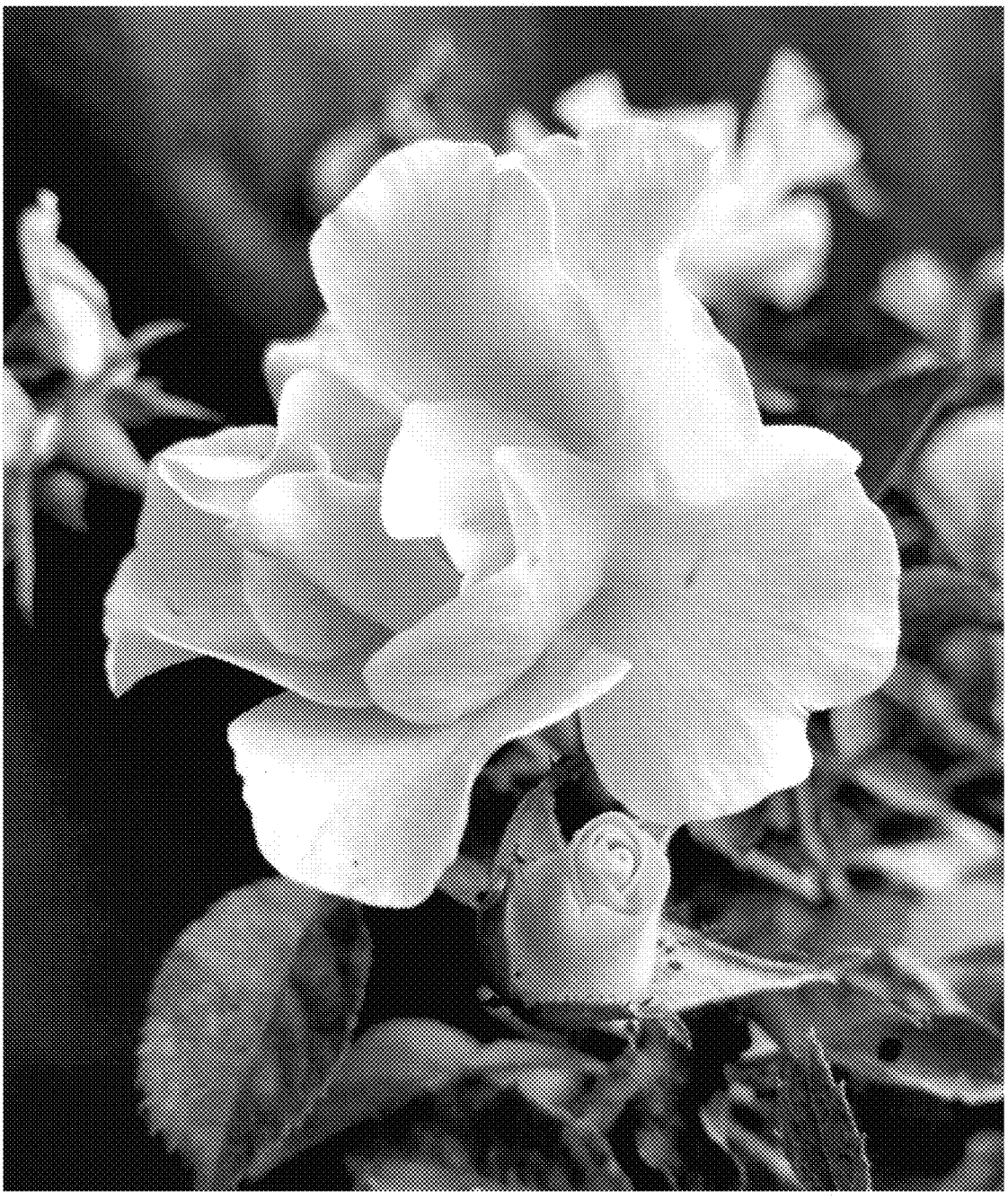

Botanical classification: *Rosa hybrida.*
Variety denomination: 'VLR12062'.

CROSS REFERENCE TO A RELATED APPLICATION

This application claims priority to a Canadian Plant Breeder's Rights Application No. 22-11139 filed on Dec. 6, 2022, under 35 U.S.C. 119(f), the entire contents of which is incorporated by reference herein. The Applicant received the information for the Plant breeders' rights application indirectly from the Inventors.

BACKGROUND OF THE INVENTION

The present invention relates to a new and distinct cultivar of *Rosa* of hybrid origin. The new cultivar will be referred to hereafter by its cultivar name, 'VLR12062'. 'VLR12062' is a new cultivar of hybrid shrub rose grown for use as a container and landscape plant.

The new cultivar was derived from a breeding program by the Inventors in Vineland Station, Ontario, Canada. The goal of the breeding was to produce a new cultivar of rose with cold hardiness to U.S.D.A. Zone 4 and resistance to black spot disease. The Inventor made a cross in 2012 between unpatented and unnamed plants from their breeding program; *Rosa* accession No. 6 as the female parent and accession No. 564 as the male parent. 'VLR12062' was selected in 2014 as a single unique plant amongst the resulting seedlings that resulted from the above crosses.

Asexual propagation of the new cultivar was first accomplished by stem cuttings under the direction the Inventors in September 2015 in Vineland Station, Ontario, Canada. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'VLR12062' as a unique cultivar of *Rosa.*

1. 'VLR12062' exhibits flowers that are yellow in color with margins that are light pink in color and may become suffused with red when grown in cold temperatures.
2. 'VLR12062' exhibits flowers that are medium in size.
3. 'VLR12062' exhibits semi-double flowers.
4. 'VLR12062' exhibits mildly fragrant flowers.
5. 'VLR12062' exhibits an upright, bushy plant habit.
6. 'VLR12062' exhibits foliage that is slightly glossy and dark green in color.

7. 'VLR12062' exhibits good resistance to black spot disease.
8. 'VLR12062' exhibits cold hardiness at least to U.S.D.A. Zone 4.

The female parent of 'VLR12062' differs from 'VLR12062' in having flowers that single and red in color and leaves that are more glossy. The male parent of 'VLR12062' differs from 'VLR12062' in having flowers that are yellow in color and lack fragrance and a more compact plant habit. 'VLR12062' can be compared to the *Rosa* cultivar 'CA 33' (U.S. Plant Pat. No. 24,436), 'CA 33' differs from 'VLR12062' in having leaves that are lighter green in color, inflorescences that are deeper gold in color, and less resistance to black rot.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosures include website listings by NVK Nurseries, Bloomin' Easy Plants, Bron and Sons, Arbor Day, and Home Depot.

BRIEF DESCRIPTION OF THE DRA WINGS

The accompanying color photographs illustrate the overall appearance and distinct characteristics of the new *Rosa*. The photographs were taken of a 16-month-old plant of 'VLR12062' as grown outdoors in a 2-gallon container in Park Hill, OK.

The photograph in FIG. 1 provides a close-up view of an opening flower of 'VLR12062'.

Figure 2:
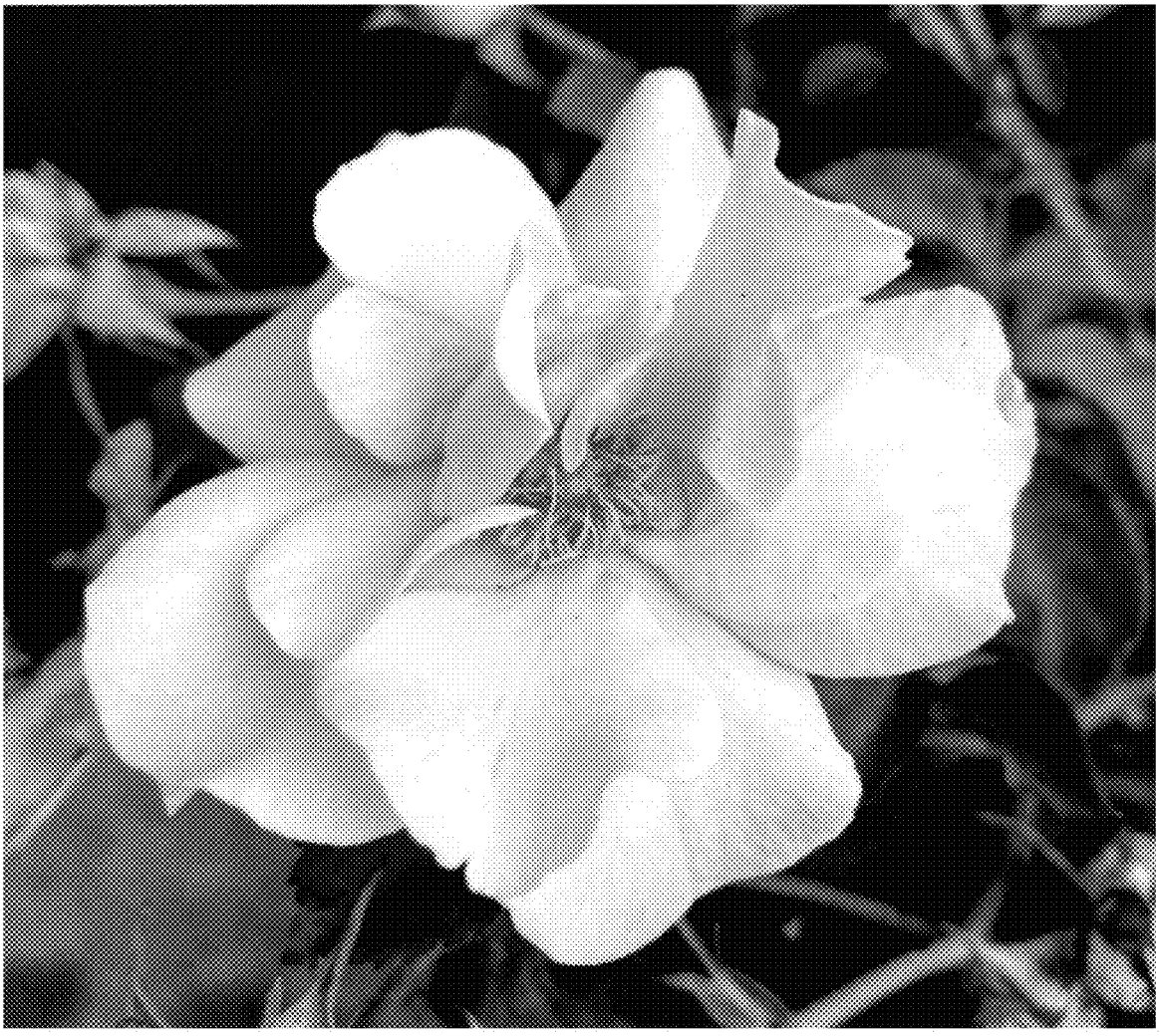

The photograph in FIG. 2 provides a close-up view of a fully open flower of 'VLR12062'.

Figure 3:
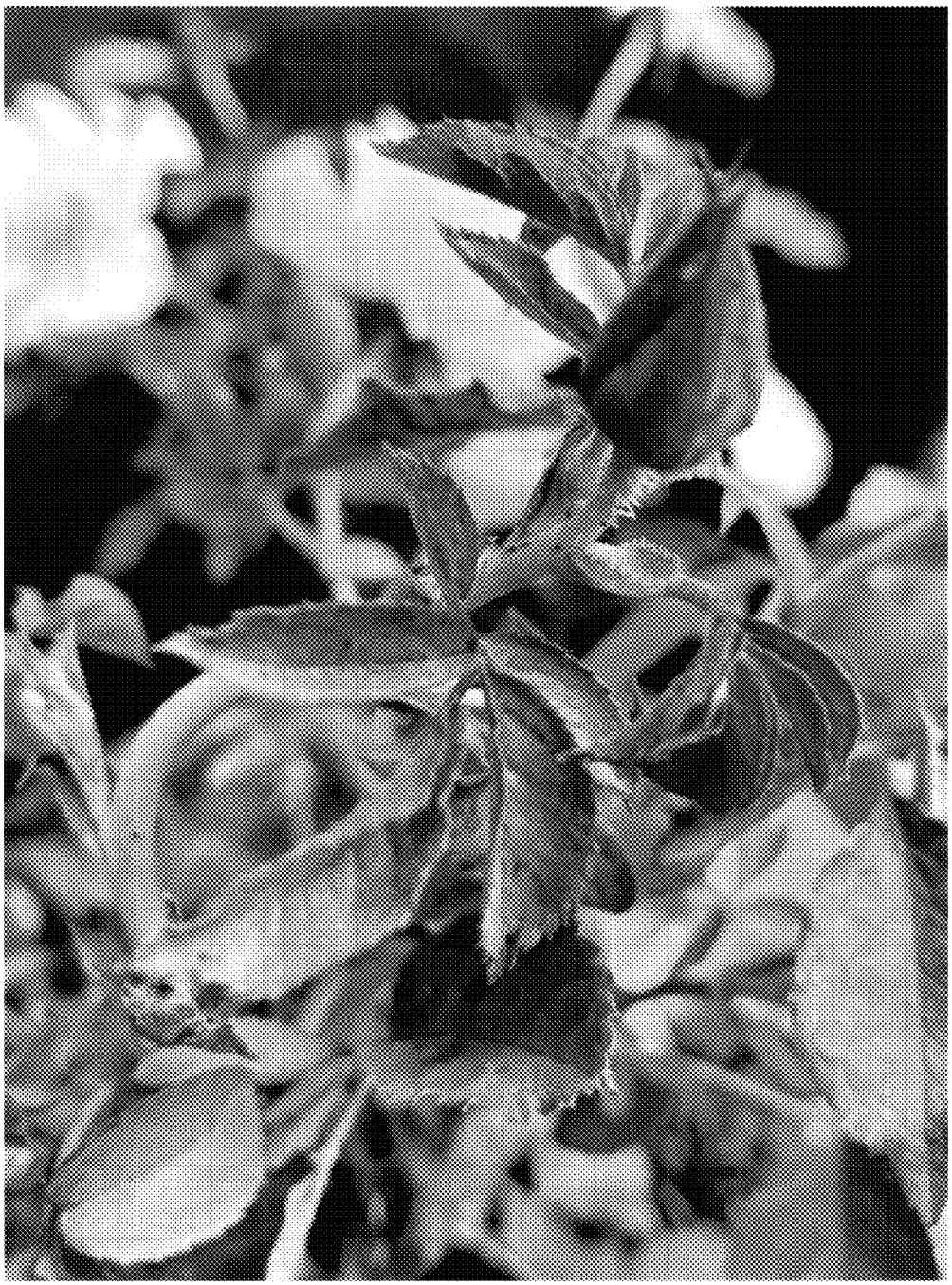

The photograph in FIG. 3 provides a close-up view of the emerging foliage of 'VLR12062'.

The colors in the photographs are as close as possible with the photographic and printing technology utilized and the color values cited in the Detailed Botanical Description accurately describe the colors of the new *Rosa*.

DETAILED BOTANICAL DESCRIPTION

The following is a detailed description of a 16-month-old plant of 'VLR12062' as grown outdoors in 2-gallon containers in Park Hill, Oklahoma. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Continuous bloom from May to September in Ontario, Canada.

*Plant type*.—Herbaceous perennial, shrub rose.

*Plant habit*.—Upright, bushy.

*Height and spread*.—An average of 35 cm in height and 57 cm in spread as a 16-month old plant and 1 m in height and width when mature in the landscape.

*Cold hardiness*.—At least to U.S.D.A. Zone 4 (canes will die back at −35° C., but will regrow in spring).

*Diseases and pests*.—Good resistant to black spot disease (caused by *Diplocarpon rosae*), no resistance or susceptibility to pests has been observed.

*Root description*.—Fibrous, 165B in color.

*Root development*.—An average of 2 to 3 weeks for root initiation with a young rooted plant produced in 8 weeks from a rooted cutting.

*Propagation*.—Stem cuttings.

*Growth rate*.—Moderate.

Stem description:

*Stem shape*.—Rounded.

*Stem color*.—Young; 144B and 142B, sometimes flushed with 185A, mature; 143B.

*Stem surface*.—Smooth, matte, covered with thorns.

*Thorns*.—Moderately covered with thorns, sharp pointed, very strong, whorled, an average of 8 per 1 cm, 160B to 160C, tips 175A, 6 mm in length, at widest point at the base 2 mm in diameter, surface is dull and glabrous.

*Stem strength*.—Strong.

*Stem size*.—Main stems; 12 cm, lateral stems 13 cm.

*Branching*.—Freely branching, held in a moderately upright to outward angle and slightly bowed, 12 main stems, 4 lateral stems per main stem.

*Internode length*.—Average of 2 cm.

Foliage description:

*Leaves*.—Pinnate division, alternate arrangement, held in a bowed, outward and downward angle, overall whole leaf shape; ovate, an average of 8 cm in length and 6 cm in width.

*Leaflets*.—5 per leaf (occasionally 3), terminal leaflet; 4.5 cm in length, 2.5 cm in width, lateral leaflets; average of 3.5 cm in length and 2 cm in width, all leaflets; ovate to elliptic in shape, cuneate base, acute apex, serrate margins, upper surface is smooth, velvety, slightly glossy and glabrous, lower surface is rugose and matte, pinnate venation pattern, color; young upper surface NN137A and 138A, slightly flushed with 178A, veins match surface color, young lower surface 178A with undertones of 138B, veins 178A, mature upper surface 147B, veins match surface color, except main vein at the base to center 144C, mature lower surface 148B, veins match surface color, except main vein 144D.

*Rachis*.—Both surfaces; flattened in shape, concave towards the center to base, up to 1.3 cm in length, 1 mm in diameter, 142C in color, surface is moderately covered with tiny thorns, sharp pointed, very strong, whorled, an average of 30 per 1 cm, 142C, tips 180A and 202A, 0.4 mm in length.

*Stipules*.—Adnate on either side of the petiole, linear in shape, 1 cm in length, 3 mm in width, both surfaces are slightly glossy, glabrous, margins are serrate and densely covered with minute pubescent hairs, 0.2 mm in length, matching surface colors, color; upper surface 138A, margins 177A, lower surface 138B.

*Petioles*.—(Terminal and lateral) both surfaces; flattened in shape, concave towards the center to base, up to 2 cm in length, 1 mm in diameter, 142C in color, surface is moderately covered with tiny thorns, sharp pointed, very strong, whorled, an average of 30 per 1 cm, 142C, tips 180A and 202A, 0.4 mm in length.

*Petiolule*.—Both surfaces; Flattened in shape, up to 2 mm in length, 0.5 mm in diameter, 142C, flushed with 180A in color, surface is matte and moderately covered with tiny hairs; 0.4 mm in length, matching surface color.

Inflorescence description:

*Inflorescence type*.—Raceme of single flowers on stem terminus.

*Inflorescence shape*.—Ovate and flattened.

*Inflorescence size*.—Up to 13 cm in height and 21 cm in diameter.

*Flower number*.—An average of 6 open flowers per raceme, average of 45 buds and flowers per plant.

*Flower fragrance*.—Faint, pleasant rose scent.

*Flower longevity*.—Raceme lasts about 20 days, individual flowers 4 to 5 days.

*Flower type*.—Semi-double, rotate.

*Flower size*.—Up to 6 cm in diameter and 3 mm in depth.

*Flower aspect*.—Upright at full bloom to outwards.

*Peduncles*.—Round in shape, strong, up to 4.5 cm in length, 1 mm in diameter, color; 142C, randomly flushed to fully flushed with 184C, surface is moderately covered with tiny thorns, sharp pointed, very strong, whorled, an average of 20 per 1 cm, 187A, 1 mm in length.

*Flower buds*.—Broadly ovate in shape, up to 1.5 cm in length, 1 cm in diameter, glabrous surface, color; before burst 138A, flushed with 184A at the top, after burst 138A, flushed with 184A on the sepals, petal portion visible 20A to 20B.

*Sepals*.—5, rotate in arrangement, lanceolate in shape, acuminate apex, truncate base, entire margins, 1.8 cm in length and 8 mm in width, upper surface; 143A in color, sheen and densely covered with matted, woolly hairs, NN155D in color, lower surface; 144C and 143B in color, glossy and densely covered with soft, translucent hairs mainly on the margins; 0.4 mm in length, NN155D in color.

*Petals*.—8 to 14, persistent, rotate in arrangement, broadly obovate in shape, up to 2.5 cm in length and width, obtuse to rounded apex, entire to slightly undulate margins, cuneate to cordate base, both surfaces are velvety, glabrous and matte, color: upper and lower surface when opening; 10A, upper surface when fully open; 11C to 11D, top lightly flushed with 49B, base flushed with 9A, fading to NN155C top flushed with 52B to 52D before drop, lower surface when fully open; 8C to 8D, base lightly flushed with 9A, may become suffused with 34A to 34B when grown under cold temperatures, fading to NN155C before drop.

*Bracts*.—Simple, linear in shape, up to 2.5 cm in length, 4 mm in width, acute apex, serrate margins, base is cuneate, both surfaces glossy and densely covered with translucent and sheen woolly hairs, matching surface color, color; upper surface NN137A and 138A, slightly flushed with 178A, veins match surface color, lower surface 178A with undertones of 138B, veins 178A.

*Receptacle*.—Round, 5 mm in length and diameter, glossy surface, color; 141C, sometimes flushed with 184C.

Reproductive organs:

*Gynoecium*.—Pistil; 1, syncarpous, average of 15 styles with stigmas, stigma is club-shaped, 1 mm in diameter, 21A in color, style; up to 6 mm in length, 0.4 mm in diameter, 155A in color, surface; sheen, densely covered with long thin woolly hairs, 1 mm in length, 155A in color, ovary; oval, 2 mm in length, 1 mm in width, 155B in color, sheen, surface very densely covered with long thin woolly hairs, up to 1.5 mm in length, 155A in color.

*Androecium*.—An average of 70 stamens, filaments; up to 1 cm in length, 13A in color, anthers; kidney shaped, curved, basifixed, an average of 1 mm in length and 0.7 mm in width, N200A in color, pollen; moderate in quantity and 25A in color.

*Fruit and seed*.—None observed to date.

It is claimed:

1. A new and distinct cultivar of *Rosa* plant named 'VLR12062' as herein illustrated and described.

* * * * *